United States Patent
Friedrich et al.

(10) Patent No.: US 6,794,530 B1
(45) Date of Patent: *Sep. 21, 2004

(54) PROCESS FOR MAKING γ-ALKOXYAMINES (75) Inventors: Wolfgang Friedrich, Speyer (DE); Heinz-Josef Kneuper, Mannheim (DE); Karsten Eller, Ludwigshafen (DE); Andreas Henne, Neustadt (DE); Rolf Lebkücher, Mannheim (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,242

(22) Filed: Jan. 22, 1999

(30) Foreign Application Priority Data

Jan. 30, 1998 (DE) .......................... 198 03 515

(51) Int. Cl.⁷ .......................... C07C 209/48
(52) U.S. Cl. .................................. 558/450
(58) Field of Search ........................ 558/450

(56) References Cited

U.S. PATENT DOCUMENTS

| | | | |
|---|---|---|---|
| 3,493,598 A | 2/1970 | Papesch | 260/465 |
| 4,231,956 A | * 11/1980 | Sullivan, III et al. | 260/465.8 R |
| 4,617,154 A | * 10/1986 | Green | 558/450 |
| 4,709,072 A | 11/1987 | Merger et al. | 558/450 |
| 5,196,589 A | 3/1993 | O'Lenick et al. | 564/493 |

FOREIGN PATENT DOCUMENTS

| | | |
|---|---|---|
| DE | 2061804 | 6/1972 |
| DE | 2136884 | 2/1973 |
| DE | 2217494 | 10/1973 |
| DE | 3522906 | 1/1987 |
| JP | 5025201 | 2/1993 |

OTHER PUBLICATIONS

Cyanoethylation, Chap. 2, Brunson, 79–135, Org. Reactions, vol. 5, 1949.
Organic Reactions, vol. V, Adams v–vi, 1949.
Houber–Weyl, Band 11/1, p. 341 (4 Ed 1957).
J.Org.Chem. vol. 38, No. 20, 1973.
Olefins From Amines . . . Cope 317–493, Chapter 5 (year not available).
J.Am. Chem. Soc., 67, 1505–6 (1945) Utermohlen.
Amines II. Reactions, Chap. 23, 854 (year not available).

* cited by examiner

Primary Examiner—Laura L. Stockton
(74) Attorney, Agent, or Firm—Keil & Weinkauf (57) ABSTRACT

A process for preparing β-alkoxynitriles by reacting α,β-unsaturated nitriles with monohydric, dihydric or trihydric alcohols in the presence of basic catalysts at from −20 to +200° C. comprises using a diazabicycloalkene catalyst of the formula I

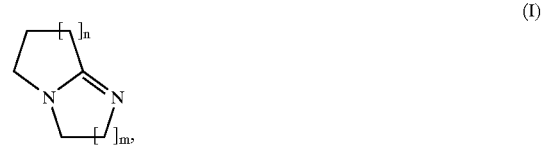

(I)

where from 1 to 4 hydrogen atoms may be independently replaced by the radicals $R^1$ to $R^4$, in which case
$R^1$, $R^2$, $R^3$, $R^4$ are each $C_{1-20}$-alkyl, $C_{6-20}$-aryl or $C_{7-20}$-arylalkyl, and
n and m are each an integer from 1 to 6.

5 Claims, 3 Drawing Sheets

Temperature diagram for ACN addition to diethylene glycol

PROCESS FOR MAKING γ-ALKOXYAMINES

This invention relates to a process for preparing β-alkoxy-nitriles by reacting low molecular weight α,β-unsaturated nitriles, having up to 40 carbon atoms for example, with monohydric, dihydric or trihydric alcohols, each having a molar mass of up to $2.5 \times 10^3$ g/mol for example, in the presence of basic catalysts at from −20 to +200° C.

The 1,4-addition of monohydric or polyhydric alcohols to α,β-unsaturated nitriles is a known reaction which is classified as a Michael-type addition in J. March, Advanced Organic Chemistry, $3^{rd}$ Ed., page 665, J. Wiley & Sons, 1985, because of the reaction mechanism.

As observed in H. A. Bruson, Organic Reactions, Vol. 5, Chapt. 2, page 89, R. Adams (Ed.), J. Wiley, 1949, for example, this addition reaction usually requires a basic catalyst in order that satisfactory reaction rates may be obtained.

In many cases, the reaction mixtures comprising the 1,4-addition product are directly, without purification, converted into γ-alkoxyamines in a second process step by subsequent catalytic hydrogenation. Existing processes are surveyed, for example, in Houben-Weyl, Methoden der organischen Chemie, volume 11/1, pages 341 et seq., 4th edition (1957).

Since the 1,4-addition of alcohols to α,β-unsaturated nitriles to form β-alkoxynitriles is reversible, the reversal of the formation of β-alkoxynitrile must be avoided in any subsequent hydrogenation in the presence of the basic catalyst (cf. also: B. A. Bruson, Organic Reactions, Vol. 5, page 90, para 3, lines 8–11). Removal prior to the hydrogenation step of the small amounts of basic catalysts used is uneconomical, and they therefore have to be neutralized with an acid. In any subsequent catalytic hydrogenation of the β-alkoxynitrile, the hydrogenation catalyst must not be damaged by the 1,4-addition catalyst or its neutralized form.

Typical catalysts for the 1,4-addition of alcohols to α,β-unsaturated nitriles include, for example, the metals sodium and potassium or their oxides, hydroxides, hydrides, cyanides and amides, as likewise observed in H. A. Bruson, Organic Reactions, Vol. 5, pages 81 and 89. The catalysts are customarily used in amounts of from 0.5 to 5% by weight, based on the alcohol.

W. P. Utermohlen, J. Am. Chem. Soc. 67, 1505–6, disclosed the use of sodium methoxide as basic catalyst.

The use of alkali metals entails appreciable problems with the handling of these reactive catalysts. Furthermore, alkali metal hydrides, amides and alkoxides are highly moisture-sensitive and industrially handleable only at great expense. And the chemical composition of these catalysts must be checked before use to determine their activity.

There has therefore been no shortage of attempts to find catalysts which are simple to handle on an industrial scale and, at the same time, are sufficiently active to enable the 1,4-addition reaction to take place with very high space-time yields.

DE-A-20 61 804 discloses that, inter alia, organic secondary or tertiary amines, for example piperidine or triethylamine, are useful as basic catalysts for the 1,4-addition of β-thio or β-sulfoxide-substituted ethanols to α,β-unsaturated nitriles. However, secondary amines have only limited usefulness as catalysts, since they actually react with α,β-unsaturated nitrites.

DE-A-35 22 906 discloses basic catalysts, including tertiary amines, for example triethylamine or pyridine, useful both for the preparation of 2,2'-dicyanodiethyl ether (NC—(CH$_2$)$_2$—O—(CH$_2$)$_2$—CN) from acrylonitrile and water and for the synthesis of β-alkoxynitriles from 2,2'-dicyanodiethyl ether and an alcohol.

U.S. Pat. No. 2,333,782 discloses tributylamine as catalyst for the 1,4-addition of formaldehydecyanohydrin to acrylonitrile to form β-(cyanomethoxy)propionitrile.

Basic catalysts used for the 1,4-addition of alcohols to α,β-unsaturated nitriles have frequently been quaternary tetraalkylammonium hydroxides or solutions thereof, for example benzyltrimethylammonium hydroxide (a=Triton® B), for example described in U.S. Pat. No. 3,493,598 and W. P. Utermohlen, J. Am. Chem. Soc. 67, 1505–6 (1945), or tetrakis(2-hydroxyethyl)ammonium hydroxide, described for example in DE-A-21 21 325 and DE-A-22 17 494.

As is common general knowledge, tetraalkylammonium hydroxides are thermally unstable, decomposing to form a trialkylamine, alkene and water (Hofmann elimination; see for example: R. T. Morrison and R. N. Boyd, Organic Chemistry, 6th Ed., 1992, page 854 bottom to page 855 top).

Tetraalkylammonium hydroxides having from 1 to 4 β-hydroxy substituents are likewise thermally unstable, decomposing by intra- and/or intermolecular reactions (see for example: A. R. Doumaux et al., J. Org. Chem. 38, 3630–2 (1973) and A. C. Cope et al. in 'Organic Reactions', Vol. 11, Chapter 5, Wiley, New York, 1960).

These catalysts and their solutions therefore have only limited storage life, so that their chemical composition needs to be checked too before use to determine their activity.

Owing to their thermal lability, tetraalkylammonium hydroxides used as catalysts for the 1,4-addition of alcohols to α,β-unsaturated nitrites at the customary reaction temperatures of from 35 to 140° C. (H. A. Bruson, Organic Reactions, Vol. 5, Chapt. 2, pages 89, 90 and 93) frequently give poor yields of the 1,4-addition products. Another important disadvantage is the fact that a thermally partially decomposed catalyst or its solution will cause a delay in the startup of the 1,4-addition reaction. This may cause the nitrile concentration in the reaction vessel in which the addition reaction is being carried out by addition of the α,β-unsaturated nitrile, for example acrylonitrile, to the alcohol will build up to a dangerously high level and, in the extreme case, may lead to a markedly thermic polymerization of the α,β-unsaturated nitrile.

Further disadvantages of quaternary ammonium hydroxides are their inutility for the 1,4-addition of polyhydric alcohols to α,β-unsaturated nitrites (see DE-A-22 17 494), the fact that the 1,4-addition products frequently exhibit an undesirable discoloration, and the need to neutralize them with an acid after the 1,4-addition reaction has taken place and to remove the resulting salt if the β-alkoxynitriles are to be subjected directly to a catalytic hydrogenation to form γ-alkoxyamines (see DE-A-21 36 884).

It is an object of the present invention to provide an improved process for the 1,4-addition of monohydric, dihydric or trihydric alcohols to α,β-unsaturated nitrites, which does not have the above-described disadvantages and which even makes it possible for the resulting reaction:mixture of the 1,4-addition products to be converted directly in a second process step into γ-alkoxyamines by hydrogenation in the presence of a hydrogenation catalyst without there being a need for any prior removal or neutralization of the catalyst for the 1,4-addition.

We have found that this object is achieved by a process for preparing β-alkoxynitriles:by reacting α,β-unsaturated nitrites, having from 3 to 40 carbon atoms for example, with monohydric, dihydric or trihydric alcohols, each having a molar mass of up to $2.5 \times 10^3$ g/mol for example, in the presence of basic catalysts at from −20 to +200° C., which comprises using a diazabicyclo-alkene catalyst of the formula I where from 1 to 4 hydrogen atoms may be independently replaced by the radicals $R^1$ to $R^4$,
in which case $R^1, R^2, R^3, R^4$ are each $C_{1-20}$-alkyl, $C_{6-20}$-aryl or $C_{7-20}$-arylalkyl, and
n and m are each an integer from 1 to 6.

The radicals $R^1, R^2, R^3$ and $R^4$ independently have the following meanings:

$C_{1-20}$-alkyl, such as methyl, ethyl, n-propyl, n-butyl, isobutyl, tert-butyl, n-pentyl, isopentyl, cyclopentyl, cyclopentylmethyl, n-hexyl, isohexyl, cyclohexyl, n-heptyl, isoheptyl, cyclohexylmethyl, n-octyl, isooctyl, n-nonyl, n-decyl, n-undecyl, n-.dodecyl, n-tridecyl, n-tetradecyl, n-pentadecyl, preferably $C_1$- $C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethyl-propyl, n-hexyl, isohexyl, sec-hexyl, cyclohexyl, cyclopentylmethyl, n-heptyl, isoheptyl, cyclohexylmethyl, n-octyl, isooctyl, particularly preferably $C_1$- to $C_4$-alkyl, such as methyl, ethyl, n-propyl, isopropyl, n-butyl, isobutyl, sec-butyl and tert-butyl, $C_{6-20}$-aryl, such as phenyl, 1-naphthyl, 2-naphthyl, 1-anthryl, 2-anthryl, 9-anthryl preferably phenyl, 1-naphthyl, 2-naphthyl, particularly preferably phenyl, $C_{7-20}$-arylalkyl, preferably $C_{7-12}$-phenylalkyl, such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl.

The aforementioned radicals may bear substituents that are inert under the reaction conditions, such as one or more alkyl radicals, e.g., methyl, ethyl, n-propyl, isopropyl, n-butyl, isobutyl, sec-butyl, tert-butyl.

The indices n and m in the formula I are independently integers from 1 to 6. Preferably, both n and m are integers from 1 to 3. Particularly preferably, n is 1, 2 or 3 and m is 2.

Examples of useful catalysts of the formula I are:
1,5-diazabicyclo[4.3.0]non-5-ene (DBN), 1,8-diazabicyclo-[5.4.0]undec-7-ene (DBU), 1,6-diazabicyclo[5.5.0]dodec-6-ene, 1,7-diazabicyclo[6.5.0]tridec-7-ene, 1,8-diazabicyclo-[7.4.0]tridec-8-ene, 1,8-diazabicyclo[7.5.0]tetradec-8-ene, 1,5-diazabicyclo[4.4.0]dec-5-ene (DBD), 1,8-diazabicyclo-[5.3.0]dec-7-ene, 1,10-diazabicyclo[7.3.0]dodec-9-ene, 1,10-diazabicyclo[7.4.0]tridec-9-ene, 2-methyl-1,5-diazabicyclo[4.3.0]non-5-ene, 3-methyl-1,5-diazabicyclo-[4.3.0]non-5-ene, 7-methyl-1,5-diazabicyclo[4.3.0]non-5-ene, 7-benzyl-1,5-diazabicyclo[4.3.0]non-5-ene, 11-methyl-1,8-diazabicyclo[5.4.0]undec-7-ene, 10-methyl-1,8-diazabicyclo-[5.4.0]undec-7-ene, 6-methyl-1,8-diazabicyclo[5.4.0]undec-7-ene, 6-benzyl-1,8-diazabicyclo [5.4.0]undec-7-ene, 2-methyl-1,5-diazabicyclo[4.4.0]dec-5-ene, 3-methyl-1,5-diazabicyclo-[4.4.0]dec-5-ene, 7-methyl-1,5-diazabicyclo[4.4.0]dec-5-ene, 7-benzyl-1,5-diazabicyclo[4.4.0]dec-5-ene.

Preference is given to DBN, DBD and DBU and particular preference to DBU and DBN, since these compounds are readily obtainable.

Similarly, mixtures of compounds of the formula I, for example a mixture of DBU and DBN, are useful as catalysts.

The catalysts of the formula I according to the invention, in contrast to the prior art quaternary ammonium compound catalysts, are also very useful for the complete conversion of all hydroxyl groups of di- or trihydric alcohols by 1,4-addition to α,β-unsaturated nitriles.

A further advantage of the process of the present invention is that the 1,4-addition products, i.e., the β-alkoxynitriles, exhibit significantly less discoloration than from using the prior art quaternary ammonium compound catalysts.

Diazabicycloalkenes of the formula I are preparable by various methods. An example of a known method is the addition of acrylonitrile to lactams to form cyanoethyllactams which are then hydrogenated to aminopropyllactams and finally cyclized with acid-catalyzed water elimination to form the diazabicycloalkenes (H. oediger et al., Synthesis, 591–8 (1972); H. Oediger et al., Chem. Ber. 99, 2012–16 (1966).; L. Xing-Quan, J. Nat. Gas Chem. 4, 119–27(1995)).

Prior German patent application 19752935.6 describes a process for preparing diazabicycloalkenes by reaction of lactones with diamines with water elimination.

Since diazabicycloalkenes of the formula I are strong bases which, owing to their low nucleophilicity with respect to common tertiary amines such as triethylamine or N,N-dimethylaniline, for example, occupy a special position, they are used in a whole series of organic reactions, for example in hydrogen halide elimination reactions (see above-cited references).

The excellent activity of diazabicycloalkenes of the formula I as catalysts for the 1,4-addition of alcohols to α,β-unsaturated nitrites is surprising because it was known from JP-A-5-25201/93 (Example 1) that the reaction of already 85% cyanoethylated pullulan with acrylonitrile (ACN) requires an extremely high excess of about 30 mol of ACN per mole of hydroxyl group, a huge 6% by weight of the catalyst 1,8-diazabicyclo[5.4.0]undec-7-ene (DBU) and also a long reaction time of ten days.

Pullulan is a D-maltotriose polymer having a molar mass within the range from $5 \times 10^4$ to $2 \times 10^6$ g/mol (Lit.: A. Jeanes in 'Extracellular Microbial Polysaccharides' (P. A. Sandford and A. Laskin, Ed.), pages 288, 289 and 292, Am. Chem. Soc., Washington, DC (1977)).

BRIEF DESCRIPTION OF THE DRAWINGS

FIGS. 1 and 2 compare a catalyst of the invention with a prior art catalyst and are referred to in Examples 1 and 2. FIG. 3 compares two different amounts of a catalyst of the invention: see Table 1 in Example 6.

The process of the present invention can be carried out as follows:

For a batchwise procedure, the alcohol is charged to a reaction vessel under atmospheric or superatmospheric pressure together with the catalyst of the formula I, optionally dissolved in an inert solvent, and the α,β-unsaturated nitrile is metered in. Examples of suitable reaction vessels include stirred reactors and stirred-tank batteries.

A continuous process is carried out using, for example, stirred-tank, loop or tubular reactors, or a combination thereof, optionally each at different temperatures, into which the two reactants and the catalyst of the formula I are transported.

A continuous procedure is preferable from the safety aspect.

The high activity of the catalysts of the formula I shows that there is no delay before the reaction starts up with the evolution of heat and the formation of the β-alkoxynitriles, thus keeping the concentration of α,β-unsaturated nitrile in the reaction vessel very low, since it immediately reacts with the alcohol. This is, on the one hand, beneficial for the selectivity of the 1,4-addition reaction and, on the other avoids the above-described safety risks due to polymerizations of unconverted α,β-unsaturated nitrile.

The catalyst is advantageously used in an amount of from 0.05 to 5% by weight, based on the alcohol. Lower quantities require longer reaction times or higher reaction temperatures; larger quantities are less interesting for economic reasons. The catalysts of the present invention are notable for high activity and hence may also be used in small amounts of from 0.05 to 3%, preferably from 0.05 to 2%, particularly preferably from 0.1 to 1.5%, by weight, based on the alcohol.

The two starting materials, the alcohol and the α,β-unsaturated nitrile, are customarily used in a molar ratio such that the molar ratio of hydroxyl group to be reacted to α,β-unsaturated nitrile is within the range from 1:0.5 to 1:10, preferably within the range from 1:0.8 to 1:2, particularly preferably within the range from 1:0.9 to 1:1.2. If less than 1 mol of α,β-unsaturated nitrile is used per mole of hydroxyl group to be reacted, incomplete conversion of this hydroxyl group is obtained and, after the reaction has ended, virtually all the free α,β-unsaturated nitrile has gone, which can have safety advantages. True, a molar excess of α,β-unsaturated nitrile based on hydroxyl groups present will bring about complete conversion of the alcohol, but entails problems with the workup of the reaction effluents, since these will still include usually toxic, unconverted α,β-unsaturated nitrites.

The catalysts of the formula I according to the present invention are additionally notable for bringing about complete alcohol conversion even at molar ratios of hydroxyl group to α,β-unsaturated nitrile within the range from 1:1 to 1:1.1, whereas less suitable addition catalysts require a larger molar excess of α,β-unsaturated nitrile.

If dihydric or trihydric alcohols are to be added to α,β-unsaturated nitriles, the reaction conditions may be controlled in such a way, for example through choice of the molar ratio of alcohol to α,β-unsaturated nitrile, that mono-, bis- or tris-1,4-addition products are obtained. For instance, diethylene glycol can be reacted with one mole equivalent of acrylonitrile to obtain the product having the formula HO—$(CH_2)_2$—O—$(CH_2)_2$—O—$(CH_2)_2$—CN.

Examples of inert solvents suitable for the reaction are ethers, such as tetrahydrofuran (THF), methyl tert-butyl ether (MTBE), or 1,4-dioxane, or N-methylpyrrolidone (NMP), N,N-dimethylformamide (DMF), dimethyl sulfoxide (DMSO), sulfolane, preferably THF or NMP. Mixtures of suitable solvents can also be used.

In many cases, as in the illustrative reaction embodiments, the reaction can be carried out without a solvent being present

The reaction temperature depends on the reactivity of the alcohol and α,β-unsaturated nitrile used, the melting points and the volatility of the starting materials. Suitable reaction temperatures are generally within the range from −20 to +200° C., the reaction being carried out at superatmospheric pressure in certain circumstances. Preference is given to reaction temperatures from 0 to 150° C., particularly preferably from 25 to 100° C.

If the reaction is carried out in the absence of a solvent, the reaction temperature is set sufficiently high for the alcohol used to be present in liquid form.

The (absolute) reaction pressure is generally within the range from 0.05 to 2 MPa, preferably from 0.09 to 1 MPa, particularly preferably atmospheric pressure.

According to the invention, the reaction of the alcohols with the α,β-unsaturated nitrites is generally carried out with residence times of from 15 min to 10 h. Preference is given to residence times of from 1 to 5 h, particularly preferably from 1 to 3 h. The higher the reaction temperature chosen, the shorter in general the residence time required.

The process of the present invention is useful, for example, for preparing β-alkoxynitriles of the formula II (II)

whale independently $R^5$, $R^6$, $R^7$ are each hydrogen, unsubstituted or halogen-, cyano-, $C_{1-30}$-alkoxy-, $C_{6-30}$-aryloxy-, $C_{2-3}$-alkenyloxy- and/or $C_{2-20}$-dialkylamino-substituted $C_{1-30}$-alkyl, $C_{2-30}$-alkenyl, $C_{3-12}$-cycloalkyl, $C_{5-12}$-cycloalkenyl, C6-20-aryl, $C_{3-15}$-hetaryl, $C_{7-20}$-arylalkyl, $C_{8-20}$-arylalkenyl, $C_{4-20}$-hetarylalkyl, $C_{7-20}$-alkylaryl, $C_{4-20}$-alkylhetaryl, Y—$(CH_2)_a$—$NR^9$—, $R^5$ and $R^6$ are jointly $(CH_2)_a$—X—$(CH_2)_b$ or jointly a halogen cyano-, $C_{1-30}$-alkoxy-, $C_{6-30}$-aryloxy-, $C_{2-3}$-alkenyloxy- and/or $C_{2-20}$-dialkylamino-substituted $C_{4-8}$-alkylene chain, $R^5$ and $R^7$ are jointly $(CH_2)_a$—X—$(CH_2)_b$ or jointly a halogen-, cyano-, $C_{1-30}$-alkoxy-, $C_{6-30}$-aryloxy-, $C_{2-3}$-alkenyloxy- and/or $C_{2-20}$-dialkylamino-substituted $C_{4-8}$-alkylene chain, X is $CH_2$, $CHR^9$, O or $NR^9$, $R^9$ is $C_{1-4}$-alkyl, $C_{6-20}$-aryl, $C_{7-20}$-alkylaryl, $C_{7-20}$-arylalkyl, Y is $C_{3-30}$-dialkylaminoalkyl, a, b are each an integer from 1 to 4, the radicals $R^5$, $R^6$ and $R^7$ together having up to 37 carbon atoms, for example, x is an integer from 1 to 3, $R^8$ is for x=1:

unsubstituted or halogen-, cyano-, hydroxyl-, $C_{1-30}$-alkoxy-, $C_{6-30}$-aryloxy-, $C_{2-3}$-alkenyloxy- and/or $C_{2-20}$-dialkylamino-substituted $C_{1-200}$-alkyl, $C_{3-200}$-alkenyl, $C_{3-200}$-alkynyl, $C_{3-12}$-cycloalkyl, $C_{5-12}$-cycloalkenyl, $C_{6-20}$-aryl, $C_{3-15}$-hetaryl, $C_{7-20}$-arylalkyl, $C_{8-20}$-arylalkenyl, $C_{4-20}$-hetarylalkyl, $C_{7-20}$-alkylaryl, $C_{4-20}$-alkylhetaryl or Y—$(CH_2)_a$—$NR^9$—$(CH_2)_{b+1}$—, $C_nH_{2n+1}$—$(NR^9$—$C_lH_{2l})_p$—$NR^9$—$C_qH_{2q}$—, alkoxyalkyl of the type $C_nH_{2n+1}$—O—$C_mH_{2m}$—, aryloxyalkyl of the type Ar—O—$C_mH_{2m}$—, where Ar is $C_{6-20}$-aryl, polyalkoxyalkyl of the type $C_nH_{2n+1}$—O—$C_mH_{2m}$—(O—$C_lH_{2l})_p$—O—$C_qH_{2q}$—, m, n, l, q are each an integer from 1 to 20, p is an integer from 0 to 50, $R^8$ is for x=2:

an unsubstituted or halogen-, cyano-, hydroxyl-, $C_{1-30}$-alkoxy-, $C_{6-30}$-aryloxy-, $C_{2-3}$-alkenyloxy- and/or $C_{2-20}$-dialkylamino-substituted $C_{2-200}$-alkane, $C_{4-200}$-alkene, $C_{4-200}$-alkyne, $C_{4-12}$-cycloalkane, $C_{5-12}$-cycloalkene, $C_{6-20}$-aromatic, $C_{3-15}$-hetaromatic, $C_{7-20}$-alkylaromatic, $C_{8-20}$-alkenylaromatic having respectively two free valences or $-C_nH_{2n}-(NR^9-C_lH_{2l})_p-NR^9-C_qH_{2q}-$, polyoxypolyalkylene of the type $C_nH_{2n}-O-C_mH_{2m}-(O-C_lH_{2l})_p-O-C_qH_{2q}-$, $R^8$ is for x=3:

an unsubstituted or halogen-, cyano-, $C_{1-30}$-alkoxy-, $C_{6-30}$-aryloxy-, $C_{2-3}$-alkenyloxy- and/or $C_{2-20}$-dialkylamino-substituted $C_{3-200}$-alkane, $C_{5-200}$-alkene, $C_{5-12}$-cycloalkane, $C_{5-12}$-cycloalkene, C6-20-aromatic, C7-20-alkylaromatic having respectively three free valences or, $-C_nH_{2n-1}-(NR^9-C_lH_{2l})_p-NR^9-C_qH_{2q}-$, polyoxypolyalkylene of the type $-C_nH_{2n-1}-O-C_mH_{2m}-(O-C_lH21)_p-O-C_qH_{2q}-$, by reaction of α,β-unsaturated nitriles having, for example, from 3 to 40 carbon atoms of the formula III (III)

with monohydric, dihydric or trihydric alcohols, for example having a molar mass of up to $2.5 \times 10^3$ g/mol, of the formula IV (IV)

The radicals $R^5$, $R^6$, $R^7$, $R^8$, $R^9$ and the designations X, Y, a, b, x, m, n, l, q and p in the compounds of the formulae II, III and IV independently have the following meanings:

$R^5$, $R^6$ and $R^7$:
identical or different,
hydrogen,
$C_{1-30}$-alkyl, preferably $C_{1-20}$-alkyl, more preferably $C_{1-12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclotron ylmethyl, n-heptyl, isoheptyl, cyclohexylmethyl, n-octyl, 2-ethylhexyl, n-nonyl, isononyl, n-decyl, isodecyl, n-undecyl, n-dodecyl and isododecyl, particularly preferably $C_{1-4}$-alkyl, such as methyl, ethyl, n-propyl, isopropyl, n-butyl, isobutyl, sec-butyl-, tert-butyl, $C_{2-30}$-alkenyl, preferably $C_{2-20}$-alkenyl, more preferably $C_{2-12}$-alkenyl, such as ethenyl, 2-propen-1-yl, 2-propen-2-yl, 2-buten-1-yl, 2-buten-2-yl, 3-buten-1-yl, 3-buten-2-yl, 2-penten-1-yl, 4-penten-1-yl, 2-hexen-1-yl, 5-hexen-1-yl, $C_{3-12}$-cycloalkyl, preferably $C_{3-8}$-cycloalkyl, such as cyclopropyl, cyclobutyl, cyclopentyl, cyclohexyl, cycloheptyl and cyclooctyl, more preferably cyclopentyl, cyclohexyl and cyclooctyl, particularly preferably cyclopentyl and cyclohexyl, $C_{5-12}$-cycloalkenyl, preferably $C_{5-8}$-cycloalkenyl, such as 1-cyclopentenyl, 3-cyclopentenyl, 1-cyclohexenyl, 3-cyclohexenyl, 1-cycloheptenyl and 1-cyclooctenyl, $C_{6-20}$-aryl, such as phenyl, 1-naphthyl, 2-naphthyl, 1-anthryl, 2-anthryl, 9-anthryl more preferably phenyl, 1-naphthyl, 2-naphthyl, particularly preferably phenyl, $C_{3-15}$-hetaryl, such as: 2-pyridinyl, 3-pyridinyl, 4-pyridinyl, pyrazinyl, pyrrol-3-yl, imidazol-2-yl, 2-furanyl and 3-furanyl, $C_{7-20}$-arylalkyl, more preferably $C_{7-12}$-phenylalkyl, such as benzyl, 1-phenethyl, 2-phenethyl, 4-tert-butylphenylmethyl, 1-phenylpropyl, 2-phenylpropyl, 3-phenylpropyl, 1-phenyl-butyl, 2-phenylbutyl, 3-phenylbutyl and 4-phenylbutyl, particularly preferably benzyl, 1-phenethyl and 2-phenethyl, $C_{8-20}$-arylalkenyl, more preferably $C_{8-12}$-phenylalkenyl, such as 1-phenethenyl, 2-phenethenyl, 3-phenyl-1-propen-2-yl and 3-phenyl-1-propen-1-yl, $C_{4-20}$-hetarylalkyl, such as pyrid-2-ylmethyl, furan-2-ylmethyl, pyrrol-3-ylmethyl and imidazol-2-ylmethyl, $C_{7-20}$-alkylaryl, more preferably $C_{7-12}$-alkylphenyl, such as 2-methylphenyl, 3-methylphenyl, 2,4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-isopropyl-phenyl, 3-isopropylphenyl, 4-isopropylphenyl and 4-tert-butylphenyl, $C_{4-20}$-alkylhetaryl, such as 2-methyl-3-pyridinyl, 4-methylimidazol-2-yl, 4,5-dimethylimidazol-2-yl, 3-methyl-2-furanyl and 5methyl-2-pyrazinyl, $Y-(CH_2)_a-NR^9-$, where Y, a and $R^9$ are each as defined below, such as $(CH_3)_2N-(CH_2)_2-NCH_3-$, $(CH_3)_2N-(CH_2)_3-NCH_3-$, $(CH_3)_2N-(CH_2)_4-NCH_3-$, $R^5$ and $R^6$:
together $(CH_2)_a-X-(CH_2)_b$, where a, b and X are each as defined below, such as $-(CH_2)_3-$, $-(CH_2)_4-$, $-(CH_2)_5-$, $-(CH_2)_6-$, $-(CH_2)_2-O-(CH_2)_2-$, $-CH_2-O-(CH_2)_2-$, $-CH_2-CHCH_3-(CH_2)_2-$, $-(CH_2)_2-NCH_3-(CH_2)_2-$, $-(CH_2)_2-N(CH_2Ph)-(CH_2)_2-$, $R^5$ and $R^7$:
together $(CH_2)_a-X-(CH_2)_b$, where a, b and X are each as defined below, such as $-(CH_2)_3-$, $-(CH_2)_4-$, $-(CH_2)_5-$, $-(CH_2)_6-$, $-(CH_2)_2-O-(CH_2)_2-$, $-CH_2-O-(CH_2)_2-$, $-CH_2-O-CH_2-$, $-CH_2-CHCH_3-(CH_2)_2-$, $-(CH_2)_2-NCH_3-(CH_2)_2-$, $-(CH_2)_2-N(CH_2Ph)-(CH_2)_2-$, $R^9$:
$C_{1-4}$-alkyl, such as methyl, ethyl, n-propyl, isopropyl, n-butyl, isobutyl, sec-butyl, tert-butyl, $C_{6-20}$-aryl as defined above, $C_{7-20}$-alkylaryl as defined above, or $C_{7-20}$-arylalkyl as defined above, X:
$CH_2$, $CHR^9$, O or $NR^9$, Y:
$C_{3-30}$-dialkylaminoalkyl, preferably $C_{3-20}$-dialkylaminoalkyl, particularly preferably $C_{3-12}$-dialkylaminoalkyl, such as dimethylaminomethyl, diethylaminomethyl, diisopropylaminomethyl, di-n-propylaminomethyl, 2-dimethylaminoethyl, 2-diethylaminoethyl, 2-di-n-propylaminoethyl and 2-di-iso-propylaminoethyl, $(R^9)_2N-(CH_2)_a$, a, b:
independently,
an integer from 1 to 4, preferably 1, 2 or 3, the radicals $R^5$, $R^6$ and $R^7$ together having up to 37 carbon atoms, for example, x:

an integer from 1 to 3, preferably 1 or 2, $R^8$:

for x=1:

- $C_{1-200}$-alkyl, preferably $C_{1-20}$-alkyl, more preferably $C_{1-12}$-alkyl, such as methyl, ethyl, n-propyl, isopropyl, n-butyl, isobutyl, sec-butyl, tert-butyl, n-pentyl, isopentyl, sec-pentyl, neo-pentyl, 2-methyl-but-2-yl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl and isododecyl, particularly preferably $C_{1-8}$-alkyl, such as methyl, ethyl, n-propyl, isopropyl, n-butyl, isobutyl, sec-butyl, tert-butyl, 2-ethylhexyl, and also more preferably $C_{40-200}$-alkyl, such as polybutyl, polyisobutyl, polypropyl, polyisopropyl and polyethyl, polybutylmethyl, polyisobutylmethyl, polypropylmethyl, polyisopropylmethyl and polyethylmethyl,
- $C_{3-200}$-alkenyl, preferably $C_{3-20}$-alkenyl, more preferably $C_{3-12}$-alkenyl, such as 2-propen-1-yl, 2-buten-1-yl, 3-buten-1-yl, 1-buten-3-yl, 1-buten-3-methyl-3-yl, 2-penten-1-yl, 4-penten-1-yl, 2-hexen-1-yl, 5-hexen-1-yl,
- $C_{3-200}$-alkynyl, preferably $C_{3-20}$-alkynyl, more preferably $C_{3-12}$-alkynyl, such as 2-propyn-1-yl, 2-butyn-1-yl, 3-butyn-1-yl, 1-butyn-3-yl, 1-butyn-3-methyl-3-yl, 2-pentyn-1-yl, 4-pentyn-1-yl, 2-hexyn-1-yl, 5-hexyn-1-yl, 1-pentyn-3-methyl-3-yl, 1-octyn-4-ethyl-3-yl,
- $C_{3-12}$-cycloalkyl, as defined above,
- $C_{5-12}$-cycloalkenyl, as defined above,
- $C_{6-20}$-aryl, as defined above,
- $C_{3-5}$-hetaryl, as defined above,
- $C_{7-20}$-arylalkyl, as defined above,
- $C_{8-20}$-arylalkenyl, as;defined above,
- $C_{4-20}$-hetarylalkyl, as defined above,
- $C_{7-20}$-alkylaryl, as defined above,
- $C_{4-20}$-alkylhetaryl, as defined above,
- $Y-(CH_2)_a-NR^9-(CH_2)_{b+1}-$, where Y, $R^9$, a and b are each as defined above, such as $(CH_3)_2N-(CH_2)_2-NCH_3-(CH_2)_2-$, $(CH_3)_2N-(CH_2)_3-NCH_3-(CPH_2)_3-$,
- $C_nH_{2n+1}-(NR^9-C_lH_{2l})_p-NR^9-C_qH_{2q}-$, where $R^9$ is as defined above and n, l, p and q are each as defined below, such as $CH_3(CH_2)_2-(NCH_3-(CH_2)_2)_5-NCH_3-(CH_2)_3-$, $CH_3-(NCH_3-(CH_2)_2)_5-NCH_3-(CH_2)_2-$,
- alkoxyalkyl of the type $C_nH_{2n+1}-O-C_mH_{2m}-$, where n and m are each as defined below, such as $CH_3OCH_2CH_2-$, $C_2H_5OCH_2CH_2-$, $CH_3O(CH_2)_4-$,
- aryloxyalkyl of the type $Ar-O-C_mH_{2m}-$, where Ar is $C_{6-20}$-aryl as defined above and m is as defined below, such as $C_6H_5OCH_2CH_2-$, $C_6H_5O(CH_2)_4-$,
- polyalkoxyalkyl of the type $C_nH_{2n+1}-O-C_mH_{2m}-(O-C_lH_{2l})_p-O-C_qH_{2q}-$, where n, m, l, p and q are each as defined below, such as $CH_3OCH_2CH_2(OCH_2CHCH_3)_3OCH_2CH_2-$, $CH_3OCH_2CH_2(OCH_2)_3 OCH_2CH_2-$, m, n, l, q:

independently an integer from 1 to 20, preferably from 1 to 10, p:

an integer from 0 to 50, preferably from 0 to 10, $R^8$:

for x 2:

- a $C_{2-200}$-alkane, preferably a $C_{2-20}$-alkane, more preferably a $C_{2-12}$-alkane, having respectively 2 free valences, such as ethane-1,2-diyl, n-propane-1,2-diyl, n-propane-1,3-diyl, n-butane-1,2-diyl, n-butane-1,3-diyl, n-butane-1,4-diyl, n-butane-2,3-diyl, 2-methylpropane-1,3-diyl, n-pentane-1,2-diyl, n-pentane-1,5-diyl, 2-methylbutane-1,4-diyl, 2,2-dimethylpropane-1,3-diyl, 1,2-dimethylpropane-1,3-diyl, n-hexane-1,2-diyl, n-hexane-1,6-diyl, n-hexane-2,5-diyl, n-heptane-1,2-diyl, n-heptane-1,7-diyl, n-octane-1,2-diyl, n-octane-1,8-diyl, 2,2,4-trimethylpentane-1,3-diyl, n-nonane-1,2-diyl, n-decane-1,2-diyl, n-decane-1,10-diyl, n-undecane-1,2-diyl, n-dodecane-1,2-diyl, particularly preferably a $C_{2-4}$-alkane having respectively 2 free valences, such as ethane-1,2-diyl, n-propane-1,2-diyl, n-propane-1,3-diyl, n-butane-1,2-diyl, n-butane-1,4-diyl, 2,2-dimethylpropane-1,3-diyl, n-hexane-1,6-diyl, and also preferably a $C_{40-200}$-alkane, such as polybutane, polyisobutane, polypropane polyisopropane and polyethane, polybutylmethane, polyisobutylmethane, polypropylmethane, polyisopropylmethane and polyethylmethane having respectively 2 free valences,
- a $C_{4-200}$-alkene, preferably a $C_{4-20}$-alkene, more preferably a $C_{4-12}$-alkene, having respectively 2 free valences, such as cis-2-butene-1,4-diyl, trans-2-butene-1,4-diyl, 3-butene-1,2-diyl, 2-pentene-1,4-diyl, 4-pentene-1,2-diyl, 2-hexene-1,6-diyl, 3-hexene-1,6diyl, 3-hexene-2,5-diyl, 5-hexene-1,2-yl, 2,5-dimethyl-3-hexene-2,5-diyl,
- a $C_{4-200}$-alkyne, preferably a $C_{4-20}$-alkyne, more preferably a $C_{4-12}$-alkyne, having respectively 2 free valences, such as 1-butyne-3,4-diyl, 2-butyne-1,4-diyl, 3-hexyne-1,6-diyl, 3-hexyne-2,5-diyl, 2,5-dimethyl-3-hexyne-2,5-diyl, 1-hexyne-5,6-diyl,
- a $C_{4-12}$-cycloalkane, preferably a $C_{4-8}$-cycloalkane, having respectively 2 free valences, such as cyclobutane-1,2-diyl, cyclopentane-1,2-diyl, cyclopentane-1,3-diyl, cyclohexane-1,2-diyl, cyclohexane-1,3-diyl, cyclohexane-1,4-diyl, cycloheptane-1,2-diyl and cyclooctane-1,2-diyl, more preferably cyclopentane-1,2-diyl, cyclohexane-1,2-diyl, cyclohexane-1,3-diyl, cyclohexane-1,4-diyl and cyclooctane-1,2-diyl, particularly preferably cyclopentane-1,2-diyl and cyclohexane-1,2-diyl,
- a $C_{5-12}$-cycloalkene, preferably a $C_{5-8}$-cycloalkene, having respectively 2 free valences, such as 1-cyclopentene-3,4-diyl, 1-cyclopentene-3,5-diyl, 1-cyclohexene-3,4-diyl, 1-cyclohexene-3,6-diyl, 1-cycloheptene-3,4-diyl, 1-cycloheptene-3,7-diyl and 1-cyclooctene-3,8-diyl,
- $C_{6-20}$-aromatic having respectively 2 free valences, such as benzene-1,2-diyl, benzene-1,3-diyl, benzene-1,4-diyl, naphthalene-1,2-diyl, naphthalene-1,4-diyl, naphthalene-1,5-diyl, naphthalene-1,8-diyl, anthracene-1,2-diyl, anthracene-1,3-diyl, anthracene-1,5-diyl,
- $C_{3-15}$-hetaromatic having respectively 2 free valences, such as pyridine-2,3-diyl, pyridine-2,4-diyl, pyrazine-2,3-diyl, pyrrole-2,3-diyl, imidazole-4,5-diyl, furan-2,3-diyl and furan-3,4-diyl,
- $C_{7-20}$-alkylaromatic having respectively 2 free valences, such as benzyl-2-yl, benzyl-4-yl, 1-methylbenzene-3, 4-diyl, 1-phenylpropane-2,3-diyl, 2-phenylpropane-1,3-diyl, 3-phenylbutane-1,2-diyl, $C_{8-20}$-alkenylaromatic having respectively 2 free valences, such as 1-vinylbenzene-3,4-diyl, $C_nH_{2n}$—$(NR^9$—$C_lH_{2l})_p$—$NR^9$—$C_qH_{2q}$—, where $R^9$, n, l, p and q are each as defined above, such as —$CH_2CH_2$($N(CH_3)CH_2CH_2)_4$—$NCH_3$—$CH_2CH_2$—, polyoxypolyalkylene of the type —$C_nH_{2n}$—O—$C_mH_{2m}$—(O—$C_lH_{2l})_p$—O—$C_qH_{2q}$, where n, m, l, p and q are each as defined above, such as, for example,: —$(CH_2)_4$—(O—$CH_2CH_2CH_2CH_2)_{26}$—, —$CH_2CH_2$($OCH_2CH_2)_2$—, $R^8$:

for x=3:

- a $C_{3-200}$-alkane, preferably a $C_{2-20}$-alkane, more preferably a $C_{2-12}$-alkane, having respectively 3 free valences, such as n-propane-1,2,3-triyl, n-butane-1,2,3-triyl, n-butane-1,3,4-triyl, 2-methylpropane-1,2,3-triyl, n-pentane-1,2,3-triyl, n-pentane-1,4,5-triyl, 2-methylbutane-1,3,4-triyl, 1,2-dimethylpropane-1,2,3-triyl, n-hexane-1,2,3-triyl, n-hexane-1,2,6-triyl, n-hexane-2,3,5-triyl. n-heptane-1,2,3-triyl, n-heptane-1,6,7-triyl, n-octane-1,2,3-triyl, n-octane-1,7,8-triyl, n-nonane-1,2,3-triyl, n-decane-1,2,3-triyl, n-decane-1,9,10-triyl, n-undecane-1,2,3-triyl, n-dodecane-1,2,3-triyl, particularly preferably, a $C_{3-5}$-alkane having respectively 3 free valences, such as n-propane-1,2,3-triyl, n-butane-1,2,3-triyl, n-butane-1,3,4-triyl,
- a $C_{5-200}$-alkene, preferably a $C_{5-20}$-alkene, more preferably a $C_{5-12}$-alkene, having respectively 3 free valences, such as 2-pentene-1,4,5-triyl, 2-hexene-1,5,6-triyl,
- a $C_{5-12}$-cycloalkane, preferably a $C_{5-8}$-cycloalkane, having respectively 3 free valences, such as cyclopentane-1,2,3-triyl, cyclopentane-1,3,4-triyl, cyclohexane-1,2,3-triyl, cyclohexane-1,3,4-triyl, cyclohexane-1,2,5-triyl,
- a $C_{5-12}$-cycloalkene, preferably a $C_{5-8}$-cycloalkene, having respectively 3 free valences, such as 1-cyclopentene-3,4,5-triyl, 1-cyclohexene-3,4,5-triyl, 1-cyclohexene-3,4,6-triyl,
- a $C_{6-20}$-aromatic having respectively 3 free valences, such as benzene-1,2,3-triyl, benzene-1,3,4-triyl, naphthalene-1,2,8-triyl, naphthalene-1,3,8-triyl, anthracene-1,2,5-triyl, $C_{7-20}$-alkylaromatic having respectively 3 free valences, such as benzyl-2,3-diyl, benzyl-3,4-diyl, 1-methylbenzene-3,4,5-triyl,-1-phenylpropane-1,2,3-diyl, 2-phenylpropane-1,2,3-triyl, $C_nH_{2n}$—$(NR^9$—$C_lH_{2l})_p$—$NR^9$—$C_qH_{2q}$—, where $R^9$, n, l, p and q are each as defined above, such as —$CH_2CH$(—)—$N(CH_3)CH_2CH_2N$—$(CH_3)CH_2CH_2$—, polyoxypolyalkylene of the type $C_nH_{2n-1}$—O—$C_mH_{2m}$—(O—$C_lH_{2l})_p$—O—$C_qH_{2q}$—, where n, m, l, p and q are each as defined above, such as —$CH_2CH$(—)—$(OCH_2CH_2)_3$—O—$C_2CH_2CH_2$—, $CH_2CH$(—)—$(OCH_2CH_2)_3$—O—$CH_2CH_2$—, —$CH_2CH$(—)$CH_2(OCH_2CH_2)_3$—O—$CH_2CH_2$—.

The radicals $R^5$, $R^6$, $R^7$ and $R^8$ may be substituted as indicated above. The number of substituents is from 0 to 5, preferably from 0 to 3, especially 0, 1 or 2, depending on the type of radical. Suitable substituents include:

halogen, such as fluorine, chlorine, bromine or iodine, preferably fluorine or chlorine, cyano: —C≡N, $C_{1-30}$-alkoxy, preferably $C_{1-8}$-alkoxy, such as methoxy, ethoxy, n-propoxy, isopropoxy, n-butoxy, isobutoxy, sec-butoxy, tert-butoxy, n-pentoxy, isopentoxy, sec-pentoxy, neo-pentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy, such as methoxy, ethoxy, n-propoxy, isopropoxy, n-butoxy, isobutoxy, sec-butoxy and tert-butoxy, $C_{6-30}$-aryloxy, such as phenoxy, 1-naphthoxy and 2-naphthoxy, preferably phenoxy, $C_{2-3}$-alkenyloxy, such as vinyloxy, 1-propenyloxy, $C_{2-20}$-dialkylamino, preferably $C_{2-12}$-dialkylamino, particularly $C_{2-8}$-dialkylamino, such as N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methyl-ethyl)-N-propylamino, N-butyl-N-propylamino, N-(1-methyl-propyl)-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methyl-ethyl)-N-(1-methylpropyl)amino, N-(1-methyl-ethyl)-N-(1-methylpropyl)amino, N-(1-methyl-ethyl)-N-(2-methylpropyl)amino, N-(1,1-dimethyl-ethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methyl-propyl)amino, diallylamino, dicyclohexylamino.

Nitriles useful for the purposes of the present invention include a multiplicity of aliphatic or aromatic α,β-unsaturated nitriles. Said α,β-unsaturated nitriles may be straight-chain or branched, contain alicyclic or heterocyclic groups and bear halogen, cyano, alkoxy, aryloxy, alkenyloxy and/or dialkylamino groups as substituents.

The number of carbon atoms in said α,β-unsaturated nitriles is not critical; it is customary to use low molecular weight α,β-unsaturated nitriles having up to 40 carbon atoms.

Examples of α,β-unsaturated nitriles of the formula III are:

acrylonitrile, methacrylonitrile, crotononitrile, 2-pentene-nitrile, β,β-dimethylacrylonitrile, β-phenylacrylonitrile. Preference is given to aliphatic α,β-unsaturated nitriles having up to 5 carbon atoms. Acrylonitrile is particularly preferred.

Useful alcohols for the purposes of the present invention include a multiplicity of aliphatic or aromatic, monohydric, dihydric or trihydric alcohols. The alcohols may be straight-chain or branched, contain alicyclic or heterocyclic groups and bear halogen, cyano, alkoxy, aryloxy, alkenyloxy and/or dialkylamino groups as substituents. The reaction rate of tertiary alcohols is generally lower than that of primary or secondary alcohols. The molar mass of the alcohols is up to 2.5×10³ g/mol, for example.

Examples of alcohols of the formula IV are:
monools, e.g., aliphatic alkanols, such as methanol, ethanol, n-propanol, isopropanol, h-butanol, isobutanol, tert-butanol, n-pentanol, 2-methyl-2-butanol, n-hexanol, cyclopentanol, cyclohexanol, 3,4-dimethylcyclohexanol, 2-ethylhexanol, 1-octanol, dodecanol, tridecanol, octadecanol, menthol, geraniol, linalool, citronellol, stearyl alcohol, palmityl alcohol, coconut alcohol, oleyl alcohol, fatty alcohols, allyl alcohol, methallyl alcohol, 4-vinyloxy-1-butanol, propargyl alcohol, n-amyl alcohol, 1-buten-3-ol, 1-butyn-3-ol, 1-butyne-3-methyl-3-ol, 1-pentyne-3-methyl-3-ol, 1-octyne-4-ethyl-3-ol, polyisobutyl alcohols, polypropyl alcohols, aromatic alcohols, such as phenol, cresols, α- or β-naphthol, benzyl alcohol, cinnamyl alcohol, 4-tert-butylbenzyl alcohol, furfuryl alcohol, alkoxyl or aryloxy-alcohols, such as 2-methoxyethanol, 2-ethoxyethanol, 2-propoxyethanol, 2-butoxyethanol, 2-phenoxyethanol, cyano alcohols, such as formaldehydecyanohydrin, β-cyanoethanol, amino alcohols, such as dimethylaminoethanol, diethylaminoethanol, 1-dimethylamino-4-pentanol, 1-diethylamino-4-pentanol, β-morpholinoethanol, triethanolamine, or the polyether alcohol formed by addition of alkylene oxides such as ethylene oxide, propylene oxide or isobutylene oxide to alcohols, e.g., methanol, ethanol, 1-butanol, such as methylhexaglycol or butyltriglycol.

Preference is given to alkanemonools and alkoxyalkanemonools having from 1 to 12 carbon atoms, such as methanol, ethanol, 2-ethylhexanol, 2-methoxyethanol and benzyl alcohol.

Diols, e.g., alkanediols, such as ethylene glycol, 1,2-propylene glycol, 1,3-propylene glycol, 2,2-dimethyl-1,3-propanediol (neopentylglycol), 1,4-butanediol, 2,3-butanediol, 1,5-pentanediol, 1,6-hexanediol, 2,5-hexanediol, 2,2,4-trimethylpentane-1,3-diol, 1,4-cyclohexanedimethanol, 2,2-bis[4-hydroxycyclohexyl] propane, di-β-hydroxyethyl ether, 2-butyne-1,4-diol, 2-butene-1,4-diol, 3-hexyne-1,6-diol, 3-hexyne-2,5-diol, 2,5-dimethyl-3-hexyne-2,5-diol, oligo- or polyalkylene glycols, such as diethylene glycol, triethylene glycol polyethylene glycol, polypropylene glycol or polytetrahydrofuran, aromatic alcohols, such as hydroquinone, or other diols, e.g., neopentylglycol monoester of hydroxypivalic acid.

Preference is given to ethylene glycol, diethylene glycol, 1,4-butanediol and polytetrahydrofuran.

Triols, e.g. alkanetriols, such as glycerol, trimethylolpropane, trimethylolethane, or the products formed by addition of alkylene oxides such as ethylene oxide or propylene oxide to triols.

The 1,4-addition products of the formula II may be recovered from the effluents of the inventive reaction of α,β-unsaturated nitriles of the formula III with alcohols of the formula IV in a conventional manner, for example by fractional rectification or crystallization. There is generally no need to remove or neutralize the catalyst of the formula I, for example with acids such as formic acid, acetic acid, 2-ethylhexanoic acid, hydrochloric acid, p-toluenesulfonic acid or phosphoric acid, first.

It has further been found :that the effluents from the inventive reaction of α,β-unsaturated nitriles of the formula III with alcohols of the formula IV, which reaction effluents include the 1,4-addition products of the formula II, can be directly subjected in a second process step to a hydrogenation in the presence of a hydrogenation catalyst to obtain γ-alkoxyamines of the formula V without there being any need for any prior costly removal or neutralization of the 1,4-addition catalyst of the formula I. Thus, the hydrogenation of the β-alkoxynitriles II in the presence of a hydrogenation catalyst can be carried out in the presence of the diazabicycloalkenes I without there being any disadvantage associated with that.

The diazabicycloalkenes I are not hydrogenated under the hydrogenation conditions customary for the β-alkoxynitriles II; if they are, for example, less volatile than the amine V, they end up in the bottom product of a rectification of the amine V and may even be recovered from there to enable the catalyst to be recycled.

The catalyst for the hydrogenation of β-alkoxynitriles II can be any common hydrogenation catalyst for this reaction, for example Raney nickel or Raney cobalt, nickel or cobalt fixed-bed catalysts, nickel or cobalt on supports and supported noble metal catalysts. The hydrogenation catalyst can be used in powder form, as suspension or in the form of a shaped article, such as an extrudate, tablet or ball.

The reaction conditions depend, inter alia, on the hydrogenation catalyst used and on the β-alkoxynitrile II used. In general, the hydrogenation of the β-alkoxynitriles II is carried out with residence times of from 20 min to 100 h at from 50 to 250° C. and from 3 to 35 MPa, optionally in the presence of an inert solvent, e.g., 1,4-dioxane, NMP, tetrahydrofuran, benzene, toluene, xylene, methanol, ethanol or butanol.

The hydrogenation may be carried out batchwise, for example in stirred autoclaves, or continuously, for example in tubular reactors.

Suitable examples of the hydrogenation of the β-alkoxynitriles II may be found in, for example, Houben-Weyl, Methoden der organischen Chemie, Volume 11/1, pages 341 et seq., 4th edition (1957), U.S. Pat. No. 5,196,589 or W. P. Utermohlen, J. Am. Chem. Soc. 67, 1505–6 (1945).

Particular preference is given to conducting the hydrogenation of β-alkoxynitriles II that comprise diazabicycloalkenes I continuously with a residence time of from 30 min to 10 h and at from 70 to 200° C. and at from 5 to 25 MPa without a solvent being present.

β-Alkoxynitriles are important intermediates for the synthesis of active compounds and dyes.

γ-Alkoxyamines are precursors for the formation of plastics, for example polyurethanes, polyamides and epoxy resins of appreciable industrial significance.

EXAMPLES

The APHA color numbers were measured according to DIN-ISO 6271.

Inventive Example 1

Methanol 52.48 g of methanol (1.64 mol) and 0.52 g of DBU were introduced as initial charge and gradually admixed at 55° C. with 80.56 g of acrylonitrile (ACN) (1.52 mol) added at 5%/min. The mixture was subsequently reacted at 55° C. for a further two hours.

The yield of 3-methoxypropionitrile as determined in the crude effluent by gas chromatography was 94%, the free acrylonitrile content was found to be 0.7% by titration, and the color number of the crude effluent was 3 APEA.

Comparative Example 1

Methanol

Inventive example 1 was repeated with 0.52 g of a 50% strength aqueous solution of tetrakis(2-hydroxyethyl)) ammonium hydroxide.

The yield of 3-methoxypropionitrile as determined in the crude effluent by gas chromatography was 94%, the free acrylonitrile content was found to be 0.4% by titration, and the color number of the crude effluent was 37 APHA.

Figure 1:
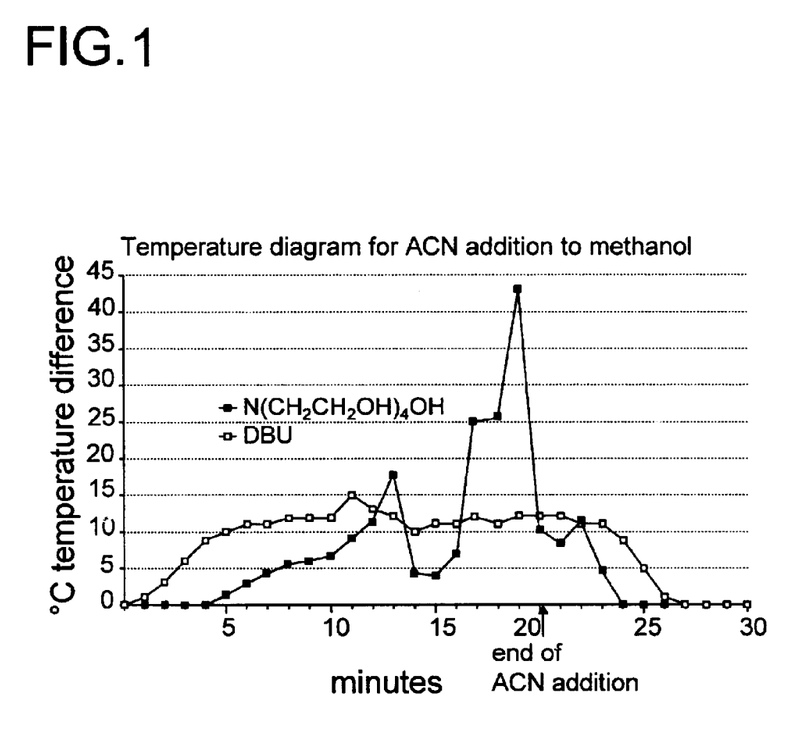
FIGS. 1, 2 and 3 are graphic representations of the temperature change during addition of acrylonitrile to the reaction system.

The temperature diagram depicted in FIG. 1 reveals that inventive example 1, utilizing DBU as catalyst, had a very uniform temperature during the addition ($\Delta T_{max}$=15° C.), whereas comparative example 1 had a temperature spike of 43° C. shortly before completion of the ACN addition. The reaction involving tetrakis(2-hydroxyethyl))ammonium hydroxide as catalyst was very slow to start up, which constitutes a considerable safety risk on an industrial scale.

Inventive Example 2

Diethylene Glycol 89.88 g of diethylene glycol (0.85 mol) and 0.90 g of DBU were introduced as initial charge and gradually admixed at 55° C. with 80.56 g of acrylonitrile (1.52 mol) added at 5%/min. The mixture was subsequently reacted at 55° C. for a further two hours.

The yield of biscyanoethylated diethylene glycol determined in the crude effluent by gas chromatography was 85.0%, the level of monocyanoethylated diethylene glycol was 13.3%, the free acrylonitrile content was 0.77% by titration, and the color number of the crude effluent was <10 APHA.

Comparative Example 2

Diethylene Glycol

Inventive example 2 was repeated with 0.85 g of a 50% strength aqueous solution of tetrakis(2-hydroxyethyl)) ammonium hydroxide.

The yield of biscyanoethylated diethylene glycol determined in the crude effluent by gas chromatography was 82.5%, the level of monocyanoethylated diethylene glycol was 14.8%, the free acrylonitrile content was 1.35%: by titration, and the color number of the crude effluent was 187 APHA.

Figure 2:
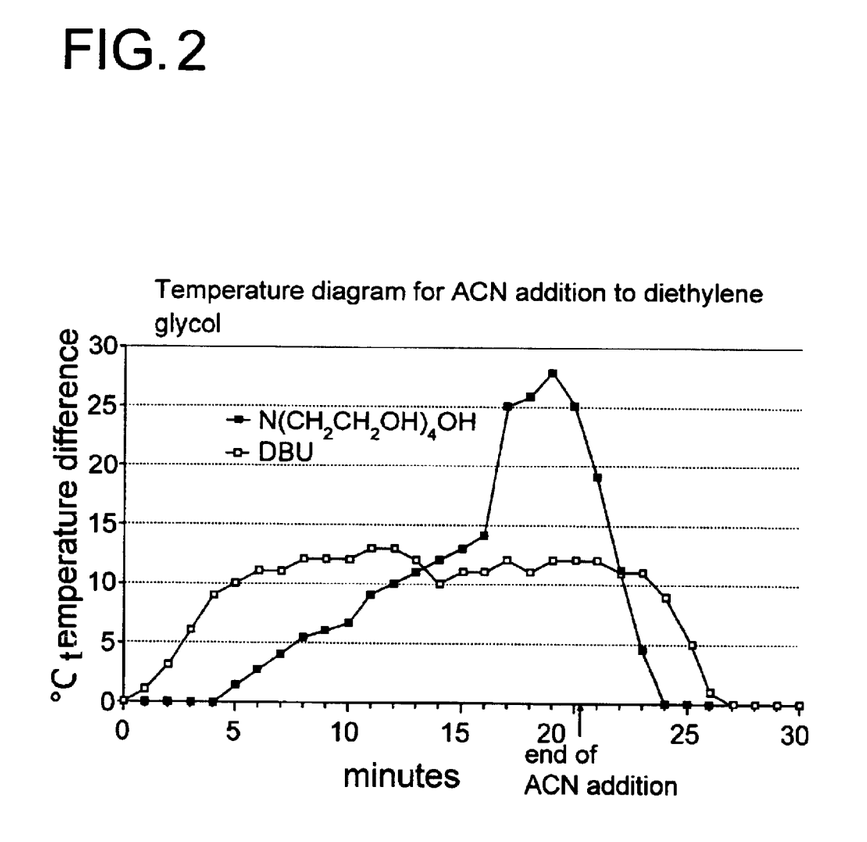

The temperature diagram depicted in FIG. 2 reveals that inventive example 2, utilizing DBU as catalyst, had a very uniform temperature during the addition ($\Delta T_{max}$=13° C.), whereas comparative example 2 had a temperature spike of 27° C. shortly before completion of the ACN addition. The reaction involving tetrakis(2-hydroxyethyl))ammonium hydroxide was very slow to start up, which constitutes a considerable safety risk on an industrial scale.

Inventive Example 3

Diethylene Glycol 85.24 g of diethylene glycol (0.80 mol) and 0.85 g of DBU were introduced as initial charge and gradually admixed at 55° C. with 80.56 g of acrylonitrile (1.52 mol) added at 5%/min. The mixture was subsequently reacted at 55° C. for a further two hours.

The yield of biscyanoethylated diethylene glycol determined in the crude effluent by gas chromatography was 90.7%, the level of monocyanoethylated diethylene glycol was 7.8%, the free acrylonitrile content was 0.33% by titration.

Comparative Example 3

Diethylene Glycol

Inventive example 3 was repeated with 0.90 g of a 50% strength aqueous solution of tetrakis(2-hydroxyethyl)) ammonium hydroxide.

The yield of biscyanoethylated diethylene glycol determined in the crude effluent by gas chromatography was 90.0%, the level of monocyanoethylated diethylene glycol was 8.9%, the free acrylonitrile content was 0.80% by titration.

Inventive Example 4

Benzyl Alcohol 88.67 g of benzyl alcohol (0.82 mol) and 0.88 g of DBU were introduced as initial charge and gradually admixed at 55° C. with 40.30 g of acrylonitrile (0.76 mol) added at 5%/min. The mixture was subsequently reacted at 55° C. for a further two hours.

The yield of 3-benzyloxypropionitrile as determined in the crude effluent by gas chromatography was 87.9%, the free acrylonitrile content was found to be 2.24% by titration, and the color number of the crude effluent was 3 APHA.

Comparative Example 4

Benzyl Alcohol 152.2 g of benzyl alcohol (1.41 mol) and 0.71 ml of a 40% strength methanolic solution of triton B (benzyltrimethylammonium hydroxide) were Introduced as initial charge and gradually admixed at 45° C. with 61.3 g of acrylonitrile (1.16 mol) added at 5%/min. The mixture was subsequently reacted at 45° C. for a further three hours. After the reaction had ended, the pH was adjusted to 6.4 with 1.2 ml of glacial acetic acid.

The yield of 3-benzyloxypropionitrile as determined in the crude effluent by gas chromatography was 83.1%, the free acrylonitrile content was found to be 0.34% by titration, and the color number of the crude effluent was 90 APHA.

Inventive Example 5

Diethylene Glycol 60.0 kg of diethylene glycol (566 mol) and 600 g of DBU were introduced as initial charge and gradually admixed at 55° C. with 58.4 kg of acrylonitrile (1102 mol) added at 5%/min. The mixture was subsequently reacted at 55° C. for a further two hours. The cyanoethylated diethylene glycol was then continuously hydrogenated at 110° C. over a cobalt catalyst, and the effluents were distilled and analyzed. 250 ml of catalyst were used and subjected at 20 MPa hydrogen pressure to 75 g h$^{-1}$ of biscyanoethyl diethylene glycol and 330 g h$^{-1}$ of NH$_3$. So the volume hourly space velocity over the catalyst was 0.3.

The yield of 4,7,10-trioxatridecane-1,13-diamine (TTD) was a constant 88% over a period of 14 days; the yield of 1,4,7-trioxaundecan-11-amine was 8%, and that of other products and distillation residue 4%.

Comparative Example 5

Diethylene Glycol

Inventive example 5 was repeated with 600 g of a 50% strength aqueous solution of tetrakis(2-hydroxyethyl)) ammonium hydroxide.

The yield of 4,7,10-trioxatridecane-1,13-diamine (TTD) was a constant 75% over a period of 21 days; the yield of 1,4,7-trioxaundecan-11-amine was 17%, and that of other products and distillation residue 8%.

Inventive Example 6

Diethylene Glycol 100.00 g of diethylene glycol (0.94 mol) were introduced as initial charge together with each of 0.2, 0.4, 0.6, 0.8 and 1.0% of DBN and gradually admixed at 55° C. with 80.56 g of acrylonitrile (1.52 mol) added at 5%/min. The mixture was subsequently reacted at 55° C. for a further two hours.

The yields of biscyanoethylated diethylene glycol (BCE-DG), of monocyanoethylated diethylene glycol (MCE-DG) and of free acrylonitrile (ACN) determined in the crude effluent by gas chromatography are shown in Table 1.

TABLE 1

| % by weight of DBN | Yield of BCE-DG [%] | Yield of MCE-DG [%] | % ACN |
| --- | --- | --- | --- |
| 0.2 | 73.4 | 21.8 | 4.0 |
| 0.4 | 75.6 | 19.9 | 4.0 |
| 0.6 | 77.0 | 18.2 | 3.4 |
| 0.8 | 78.7 | 17.1 | 2.9 |
| 1.0 | 79.8 | 16.5 | 2.7 |

Figure 3:
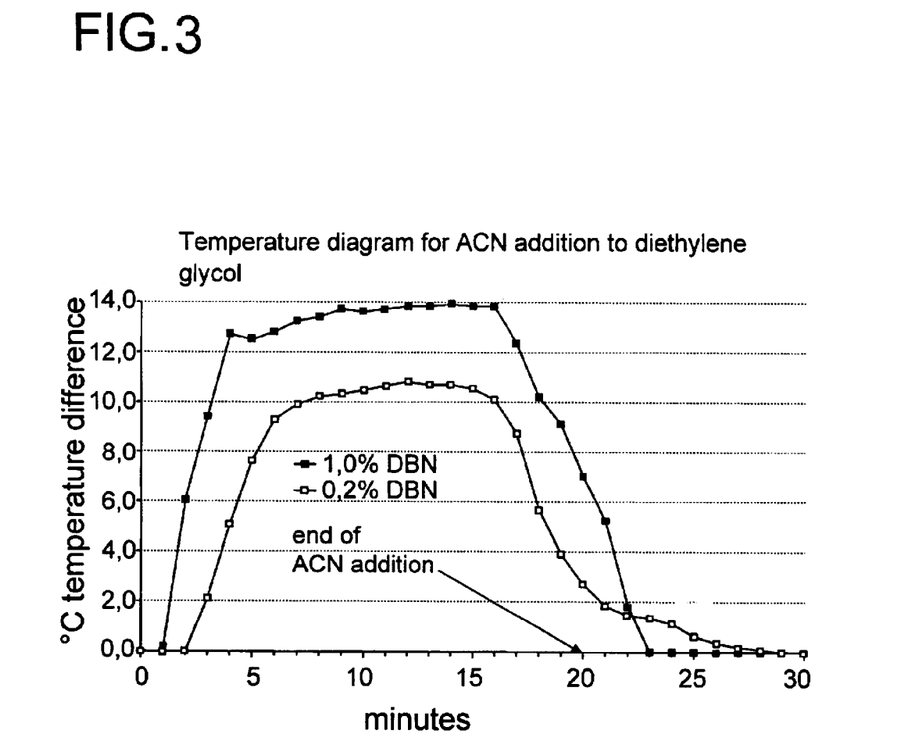

FIG. 3 shows by way of example the temperature diagram for the addition reaction involving 1% and 0.2% of DBN, similar curves being obtained with the other quantities as well.

Inventive Example 7

Methanol 48.5 kg of methanol (1515 mol) and 0.48% by weight of DBU were introduced as initial charge and gradually admixed at 55° C. with 74.3 kg of acrylonitrile (1401 mol) added at 5%/min. The mixture was subsequently reacted at 55° C. for a further two hours. The 3-methoxypropionitrile was then continuously hydrogenated at 110° C. over a cobalt catalyst, and the effluents were distilled and analyzed. 250 ml of catalyst were used and subjected at 20 MPa hydrogen pressure to 75 ml·h$^{-1}$ of methoxypropionitrile and 500 ml·h$^{-1}$ of NH$_3$. So the volume hourly space velocity over the catalyst was 0.3.

The yield of 3-methoxypropylamine determined following distillative workup was a constant 95.9% over a period of 14 days.

Inventive example 8

Methanol 48.5 kg of methanol (1515 mol) and 0.48% by weight of DBU were introduced as initial charge and gradually admixed at 55° C. with 74.3 kg of acrylonitrile (1401 mol) added at 5%/min. The mixture was subsequently reacted at 55° C. for a further two hours. The 3-methoxypropionitrile was then continuously hydrogenated at 110° C. over a cobalt catalyst, and the effluents were distilled and analyzed. 250 ml of catalyst were used and subjected at 20 MPa hydrogen pressure to 75 ml·h$^{-1}$ of methoxypropionitrile and 500 ml·h$^{-1}$ of NH$_3$. So the volume hourly space velocity over the catalyst was 0.3.

The yield of 3-methoxypropylamine determined following distillative workup was a constant 96.9% over a period of 14 days.

We claim:

1. A process for preparing a γ-alkoxyamine by a) reaction of an α, β-unsaturated nitrile with a monohydric, dihydric or trihydric alcohol in the presence of a basic catalyst at from −20 to 200° C., optionally in the presence of a solvent, to form a β-alkoxynitrile, and b) subsequent hydrogenation of the β-alkoxynitrile in the presence of a hydrogenation catalyst, optionally in the presence of a solvent, without prior removal or neutralization of said basic catalyst, which consists of using in the first step a diazabicycloalkene catalyst of the formula I (I)

where from 1 to 4 hydrogen atoms on the diazabicycloalkene nucleus may be independently replaced by the radicals R$^1$ to R$^4$, in which case R$^1$, R$^2$, R$^3$ and R$^4$ are each C$_{1\text{-}20}$-alkyl, C$_{6\text{-}20}$-aryl or C$_{7\text{-}20}$-arylalkyl, and n and m are each an integer from 1 to 6, and effecting the hydrogenation in the second step at from 50 to 250° C. in the presence of a hydrogenation catalyst and of the catalyst of the formula I.

2. A process as claimed in claim 1, wherein the catalyst used in the first step is a diazabicycloalkene of the formula Ia where from 1 to 4 hydrogen atoms on the diazabicycloalkene nucleus may be independently replaced by the radicals R$^1$ to R$^4$, in which case R$^1$, R$^2$, R$^3$ and R$^4$ are each C$_{1\text{-}20}$-alkyl, C$_{6\text{-}20}$-aryl or C$_{7\text{-}20}$-arylalkyl, and n is an integer from 1 to 3.

3. A process as claimed in claim 1, wherein the catalyst used in the first step is 1,5-diazabicyclo(4.3.0)non-5-ene (DBN), 1,5-diazabicyclo(4.4.0)dec-5-ene (DBD) or 1,8-diazabicyclo(5.4.0)undec-7-ene (DBU).

4. A process as claimed in claim 1, wherein the catalyst of the first step is used in an amount of from 0.05 to 5% by weight, based on the alcohol.

5. A process as claimed in claim 1, wherein the reaction of the first step is carried out at from 25 to 100° C.

* * * * *